United States Patent
Hussein et al.

(10) Patent No.: US 9,828,655 B2
(45) Date of Patent: Nov. 28, 2017

(54) TITANIUM ALLOYS FOR BIOMEDICAL APPLICATIONS AND FABRICATION METHODS THEREOF

(71) Applicant: King Fahd University of Petroleum and Minerals, Dhahran (SA)

(72) Inventors: Mohamed Abdrabou Hussein, Alkubar (SA); Nasser Mohammed Al-Aqeeli, Dhahran (SA)

(73) Assignee: Kind Fahd University of Petroleum and Minerals, Dhahran (SA)

( * ) Notice: Subject to any disclaimer, the term of this patent is extended or adjusted under 35 U.S.C. 154(b) by 294 days.

(21) Appl. No.: 14/845,430

(22) Filed: Sep. 4, 2015

(65) Prior Publication Data

US 2017/0067136 A1    Mar. 9, 2017

(51) Int. Cl.
| | |
|---|---|
| *C22C 14/00* | (2006.01) |
| *B22F 3/105* | (2006.01) |
| *C22C 1/04* | (2006.01) |
| *A61F 2/28* | (2006.01) |
| *A61L 27/00* | (2006.01) |

(52) U.S. Cl.
CPC ............... *C22C 14/00* (2013.01); *A61F 2/28* (2013.01); *A61L 27/00* (2013.01); *B22F 3/105* (2013.01); *C22C 1/0458* (2013.01); *B22F 2003/1051* (2013.01)

(58) Field of Classification Search
None
See application file for complete search history.

(56) References Cited

U.S. PATENT DOCUMENTS 5,573,401 A    11/1996  Davidson et al.
6,238,491 B1 *  5/2001  Davidson ............ A61F 2/30767
                                                 148/237

FOREIGN PATENT DOCUMENTS

| CN | 102312128 A | 1/2012 |
| CN | 102392150 A | 3/2012 |
| CN | 104263996 A * | 1/2015 |

OTHER PUBLICATIONS

English Translation of CN 104263996 (published Jan. 2015), obtained from Espacenet.*
You, L. et al., "First principles study of low Young's modulus Ti—Nb—Zr system", Materials Letters, vol. 80, pp. 165-167, Apr. 28, 2012.*
L. M. Zou, et al.; "Fabrication of biomedical Ti—35Nb—7Zr—5Ta alloys by mechanical alloying and spark plasma sintering"; 2012; Institute of Materials, Minerals and Mining; pp. 65-70.
Xiaojian Wang, et al.; "Porous TiNbZr alloy scaffolds for biomedical applications"; Nov. 2009; Acta Biomaterialia; vol. 5, Issue 9; 2 pp.
L. W. Ma, et al.; "Effect of thermo-mechanical treatment on superelastic behavior of Ti—19Nb—14Zr (at. %) shape memory alloy"; Jan. 2013; vol. 32; 1 p.

* cited by examiner

*Primary Examiner* — George Wyszomierski
(74) *Attorney, Agent, or Firm* — Oblon, McClelland, Maier & Neustadt, L.L.P.

(57) ABSTRACT

Alloys of titanium with 20-22 at. % niobium and 12-13 at. % zirconium. The alloys are prepared by mechanical alloying of elemental powders and densification by spark plasma sintering. The alloys have a nano-scaled, equiaxed granular structure, a microhardness of at least 650 HV and a modulus of 90-140 GPa. The inventive alloy is corrosion resistant, biocompatible, and is of a higher wear resistance and durability compared to the Ti-6Al-4V alloy. The bioactive surface of the inventive nanostructured alloy promotes a higher protein adsorption that stimulates new bone formation than other titanium-based alloys. These alloys are suitable for various biomedical and dental applications.

12 Claims, 2 Drawing Sheets

TITANIUM ALLOYS FOR BIOMEDICAL APPLICATIONS AND FABRICATION METHODS THEREOF

BACKGROUND OF THE INVENTION

Technical Field

The present invention relates to titanium alloys. More particularly, the present invention relates to titanium alloys that are alloyed with niobium and zirconium at specific atomic ratios by mechanical alloying and spark plasma sintering. These nanostructured titanium alloys are suited for but not limited to various biomedical and dental applications.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Titanium and titanium alloys are widely employed in biomedical and dental applications due to their excellent combination of biocompatibility, corrosion resistance and mechanical properties. Titanium and titanium alloys are characterized by their good fatigue strength, relatively low Young's or tension modulus and low densities which give high specific strength-to-weight ratios allowing lighter and stronger structures.

Titanium (Ti) alloys are generally classified into four main structural categories: alpha, near-alpha, alpha and beta, and beta. Alpha alloys contain neutral alloying elements such as tin and/or alpha stabilizers such as aluminum or oxygen only and are not heat treatable. Near-alpha Ti alloys, in addition to alpha stabilizers, are alloyed with 1-2% of beta stabilizers such as molybdenum, silicon or vanadium. Alpha and beta alloys are metastable and can be heat treated; they generally include some combination of both alpha and beta stabilizers. Beta Ti alloys are also metastable and heat-treatable, containing sufficient beta stabilizers to allow them to maintain the beta phase when quenched. Beta Ti alloys can also be solution treated and aged to improve strength.

Titanium is commonly alloyed with aluminum and vanadium to form alpha and beta Ti alloys as biomaterials, such as Ti-6Al-4V. However, Al and V pose toxicity problems and can adversely affect health. Ti-6Al-4V also suffers from poor shear strength and poor surface wer properties in certain loading conditions. More recently, beta Ti alloys with low Young's modulus and including niobium (Nb), zirconium (Zr) and tantalum (Ta) elements have been developed by melt solidification. Although Ti alloys incorporating these elements exhibit Young's modulus values that are closer to that of human bone (i.e. ~55 GPa), Ti, Nb, Zr and Ta are difficult to melt homogeneously by a melt casting process because these elements have a large difference in melting points and specific gravities.

Additionally, nanostructured materials are known to possess unique surfaces and exceptional mechanical properties similar to those of the human bones. It has also reported that the surface of metallic materials which possess low micron to nanophase topography can enhance and increase the adhesion of osteoblasts which are cells that create the matrix of bone. Hence, nanostructured materials are considered to be the future generation orthopedic biomaterials.

It is a non-limiting objective of the present invention to provide titanium alloys that meet the criteria for biomaterials in terms of biocompatibility, resistance to corrosion, mechanical properties and cytotoxicity. It is another object to provide a bioactive surface nanomaterial that promotes a greater amount of protein adsorption to stimulate new bone formation than conventional biomaterial structure.

BRIEF SUMMARY OF THE INVENTION

According to a first aspect, the present invention relates to an alloy comprising 20-22 at. % niobium, 12-13 at. % zirconium and ≤68 at. % titanium. The alloy is prepared by a process comprising providing an elemental powder mixture comprising 20-22 at. % niobium elemental powder, 12-13 at. % zirconium powder and ≤68 at. % titanium powder; grinding the elemental powder mixture with a grinder comprising a grinding media to form a homogeneous alloy powder; and spark plasma sintering the homogeneous alloy powder to produce the alloy.

In one embodiment, the alloy comprises 20 at. % niobium, 13 at. % zirconium and ≤67 at. % titanium.

In one embodiment the alloy is a ternary alloy and is substantially free of an additional fourth element.

In one embodiment, the elemental powder mixture is ground at a weight ratio of the grinding media to the elemental powder mixture of 8:1 to 10:1.

In one embodiment, during the grinding, the grinder is agitated at 240-360 rpm.

In one embodiment, the grinding is carried out for 10-60 h.

In one embodiment, the spark plasma sintering is carried out at 50-100 MPa, 1000° C. to 1200° C. for 5-15 min.

In one embodiment, the alloy comprises an equiaxed granular structure with an average grain size of 70-140 nm.

In one embodiment, the equiaxed granular structure of the alloy comprises a body centered cubic beta-titanium phase forming a matrix surrounding a hexagonal close packed alpha-titanium phase region.

In one embodiment, the alloy is substantially free of an omega-titanium phase.

In one embodiment, the homogeneous alloy crystalline powder comprises a body centered cubic beta-titanium phase and an average grain size of 70-140 nm.

In one embodiment, the alloy has a microhardness of 650-675 HV.

In one embodiment, the alloy has a modulus of 90-140 GPa.

The inventive alloy is corrosion resistant, biocompatibile, and has higher wear resistance and durability compared to the Ti-6Al 4V alloy According to a second aspect, the present invention relates to a device comprising the alloy of in accordance with the first aspect of the present invention.

In one or more embodiments, the device is selected from the group consisting of biomedical implants, orthopedic implants, dental implants, surgical instruments and parts thereof.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figures 1A, 1B:
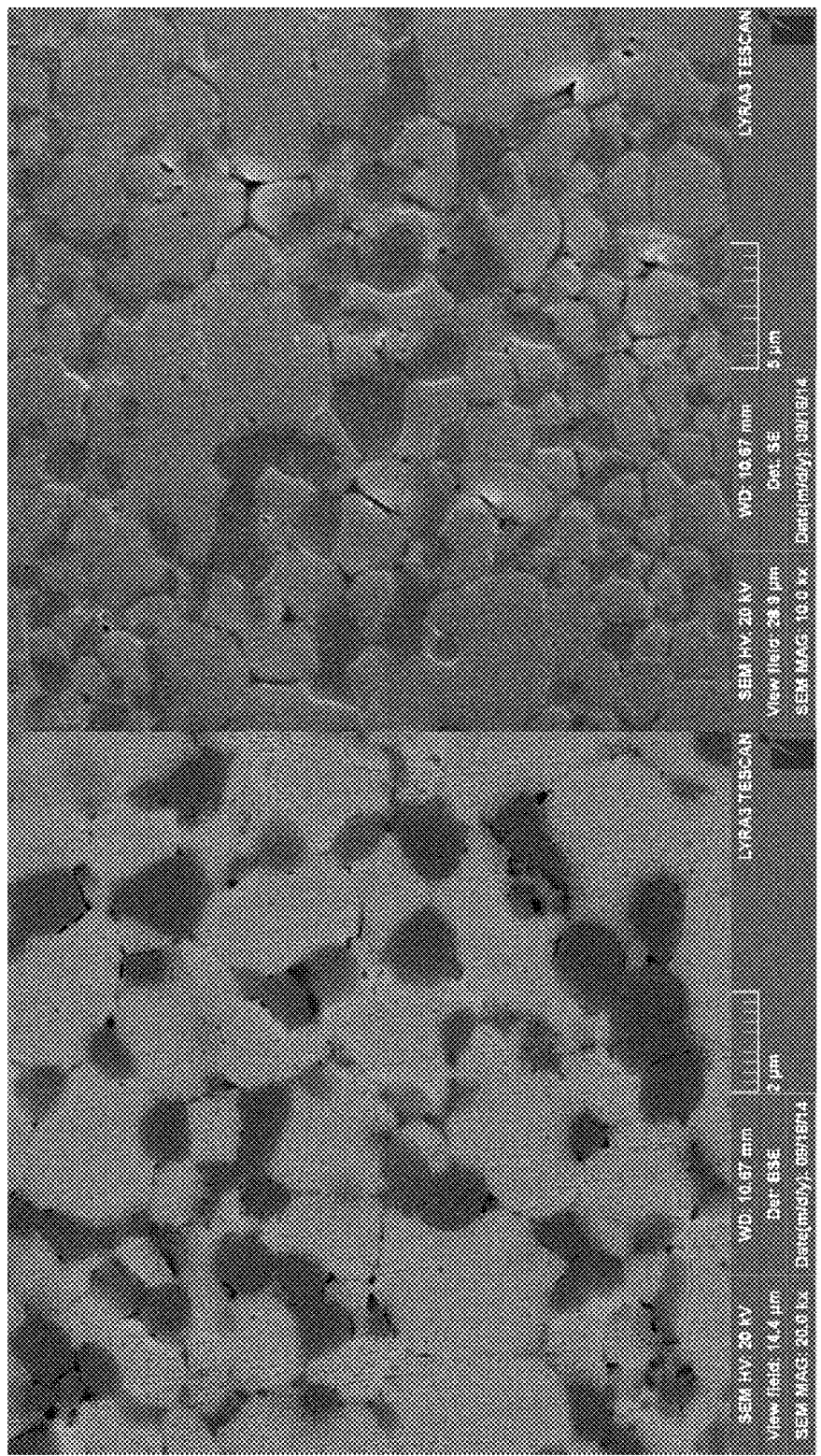
FIG. 1A is an FE-SEM image of a nanostructured titanium alloy according to one embodiment at 20 kX magnification.
FIG. 1B is an FE-SEM image of the nanostructured titanium alloy of FIG. 1A at 10 kX magnification.

Referring now to the drawings, wherein like reference numerals designate identical or corresponding parts throughout the several views.

The present disclosure relates to ternary titanium-based alloys of titanium (Ti), niobium (Nb) and zirconium (Zr) with no other additional elements that are produced by powder metallurgy followed by spark plasma sintering. These alloys contain 20-22 at. % niobium (Nb) and 12-13 at. % zirconium (Zr), with the balance being Ti (≤65-68 at. %). The atomic percentages are based on the total number of Ti, Nb and Zr atoms in the alloy. Alternatively expressed in weight percentages, these Ti alloys contain 51.3-56.5 wt. % of Ti and 17.5-19 wt. % of Zr, with the weight percentages based on the total weight of the alloy. Nb constitutes 24.5-31.2 wt. % of the alloys.

The metallurgy of Ti is dominated by the crystallographic transformation which takes place in the pure metal at 882° C. Below this temperature, pure Ti has a hexagonal close packed (hcp) structure known as alpha (α); above it, the structure is body centered cubic (bcc) and termed beta (β). The fundamental effect of alloying additions to titanium is alteration of the transformation temperature and production of a two-phase field in which both alpha and beta phases are present.

Alloying elements for Ti fall into three categories: alpha stabilizers, beta stabilizers and neutrals. As used herein, the term "alpha stabilizer" refers to an element that is added to Ti that has extensive solubility in the alpha phase characteristically and raises the alpha-to-beta transformation temperature. A non-exhaustive list of examples of alpha stabilizers include aluminum, gallium, germanium, carbon, oxygen and nitrogen. The Ti alloys provided herein are substantially free of alpha stabilizer elements.

As used herein, the term "beta stabilizer" refers to an element that is added to Ti that stabilizes the beta crystal structure and lowers the alpha-to-beta transformation temperature. Examples of beta stabilizers include but are not limited to vanadium, niobium, tantalum, molybdenum, manganese, iron, chromium, cobalt, nickel, copper and silicon. The Ti alloys provided herein are substantially free of vanadium, tantalum, molybdenum, manganese, iron, chromium, cobalt, nickel, copper and silicon. The beta stabilizer contained in these Ti alloys consists essentially of Nb.

Zr is neutral towards the alpha and beta phases of Ti and has little to no influence over the alpha-to-beta transformation temperature. Zr is added to Ti as a non-toxic element that helps to achieve and stabilize the solid solution phase of the alloy that is required for hardness, and to also impart a greater resistance to corrosion to the alloy. The Ti alloys described herein are preferably substantially free of other neutral additive alloying elements, including but not limited to palladium, indium and tin.

In one embodiment, the Ti alloy contains 20-21 at. % Nb, 12-13 at. % Zr and ≤66-68 at. % Ti, which is equivalent to 51.3-53.9 wt. % Ti, 17.5-19 wt. % Zr and 27.1-31.2 wt. % Nb.

In another embodiment, the Ti alloy contains 20 at. % Nb, 13 at. % Zr and ≤67 at. % Ti, which is equivalent to 51.3 wt. % Ti, 19 wt. Zr and 29.7 wt. % Nb.

The alloys of the present disclosure have a purity of at least 99.9%, with up to 0.1 wt. % unavoidable impurities, preferably up to 0.05 wt. %, more preferably up 0.01 wt. % of the unavoidable impurities.

Despite the enhancement in mechanical strength and corrosion resistance imparted by Nb and Zr, the addition of these alloying elements to Ti and the amounts added have been limited by conventional alloy fabrication processes such as hot wrought, melt casting and melt solidification. Specifically, the limitations are posed by the disparities in the melting points and specific gravities of Ti, Nb and Zr (at 20° C.), as summarized in Table 1, which make the solid mixture of metal elements extremely difficult to melt to form a homogeneous solid solution.

TABLE 1

| Melting points and specific gravities of Ti, Nb and Zr. | | |
|---|---|---|
| Element | Melting point (° C.) | Specific gravity at 20° C. (g/m³) |
| Titanium | 1668 | 4.55 |
| Niobium | 2469 | 8.57 |
| Zirconium | 1855 | 6.51 |

To circumvent the homogeneity problem posed by a melt manufacturing process, the Ti alloys in accordance of the present disclosure are preferably fabricated using the powder metallurgy technique. Elemental powders of Ti, Nb and Zr according to the atomic or weight percentages defined herein are physically mixed. Each of the elemental powders has a purity of at least 99%, preferably at least 99.5%, more preferably at least 99.9%. The elemental powder mixture is then loaded into the sample vial or grinding jar of a grinder or grinding machine, such as a planetary ball mill. The sample vial is generally a hollow cylindrical shell that is partially filled with grinding media such as grinding balls configured to rotate about its axis during milling. The milling or grinding mechanism is provided by the movement of the sample vial and the grinding media. In one embodiment, the sample vial is made of tungsten carbide and is partially filled with tungsten carbide balls at a ball-to-powder ratio of 10:1. The grinding media can be metallic or non-metallic. Metallic grinding media can be made of carbon steel, chrome steel, stainless steel, steel shot, tungsten carbide or any other acceptable alloy or metal. Non-metallic grinding media can be made of alumina, ceramic (steatite), glass, flint, nylon, silicon carbide, silicon nitride, tungsten carbide and other synthetic polymers. Zirconium-based grinding media such as zirconium oxide 95% or 93% that is optionally stabilized with yttrium oxide or cesium oxide and zirconium silicate are avoided. Grinding media which are spherical in shape (i.e. balls) are preferred, but grinding media of other shapes such as balcones, cylinders, diagonals, beads, pellets, pebbles and satellites are also acceptable. The media or ball to powder ratio (by weight) is in a range of 8:1 to 15:1, preferably 8:1 to 12:1, more preferably 8:1 to 10:1. In one embodiment, the ball to powder ratio is 10:1. The ball diameters are 5-20 mm, preferably 10-20 mm, more preferably 15-20 mm. In one embodiment, tungsten carbide balls are used in the ball milling process and the sample vial is also made of tungsten carbide.

Mechanical alloying processes often include the use of a process control agent such as stearic acid and methanol to minimize cold welding of the elemental powder particles and to prevent the powders from sticking to the grinding media and the vial wall. In the present disclosure, the addition of a process control agent is not required to avoid contamination of the powders.

The elemental powder mixture is blended and ground by agitating the sample vial at room temperature and under an inert atmosphere (i.e. in the presence of an inert gas such as argon or nitrogen) at 240-360 rpm (equivalent to 4 to 6 s$^{-1}$), preferably 270-360 rpm (or 4.5 to 6 s$^{-1}$), more preferably 300-360 rpm (5 to 6 s$^{-1}$). The elemental powder is ground for 8-72 h; more preferably 12-60 h, 18-60 h, 12-48 h, 12-36 h, 12-24 h, 12-30 h, 18-30 h, 24-30 h, 24-36 h, 24-48 h; more preferably 24-60 h, 30-60 h, 36-60 h, 42-60 h, 48-60 h, 54-60 h, 36 h-72 h, 42-72 h, 48-72 h, 54-72 h, 60-72 h. At the end of mechanical alloying (blending and grinding), a homogeneous alloy nanocrystalline powder of beta-Ti phase is obtained.

The obtained nanoalloy powder is then compacted and densified by spark plasma sintering (SPS). As used herein, "spark plasma sintering" (SPS), which is also known as "field assisted sintering technique" (FAST) or "pulsed electric current sintering" (PECS), is a sintering technique, in which the pulsed DC current directly passes through a graphite die, as well as the powder compact, in case of conductive samples. Joule heating has been found to play a dominant role in the densification of powder compacts, which results in achieving near theoretical density at lower sintering temperature compared to conventional sintering techniques. The heat generation is internal, in contrast to the conventional hot pressing, where the heat is provided by external heating elements. This facilitates a very high heating or cooling rate, hence the sintering process generally is very fast. The general speed of the process ensures it has the potential of densifying powders with nanosize or nanostructure while avoiding coarsening which accompanies standard densification routes.

In accordance with the present disclosure, the nanocrystalline alloy powder is fed directly in a graphite die without a pre-compaction step (e.g. by vibration or application of suitable pressure). The die containing the alloy powder can be placed directly in an SPS chamber or furnace and spacers are used if necessary. The SPS chamber is closed and the sintering is carried out under argon atmosphere with partial vacuum at a pressure of no higher than 100 MPa being applied in the chamber, preferably 50-100 MPa, more preferably 75-100 MPa. The SPS heating rate is 100° C. min$^{-1}$ to 1000° C. min$^{-1}$, preferably 500° C. min$^{-1}$ to 1000° C. min$^{-1}$, more preferably 600° C. min$^{-1}$ to 1000° C. min$^{-1}$. The SPS is carried out for 2-15 min, preferably 2-10 min, more preferably 3-8 min, 4-7 min, 4-6 min, 5-7 min, 3-5 min, 3-4 min, 4-5 min, 5-6 min and 6-7 min. The SPS temperature is no higher than 1200° C., for example, 1000° C. to 1200° C., preferably 1000° C. to 1100° C., more preferably 1100° C. to 1150° C., even more preferably 1150° C. to 1200° C. The sintering temperature and duration are kept relatively low and short respectively so as to prevent grain growth and to minimize the formation of undesired phases (i.e. phases other than beta-Ti and alpha-Ti). In spite of the low sintering temperature and short treatment, a fully consolidated and homogeneous bulk Ti alloy can be successfully formed.

The spark plasma sintering treatment does minimal to no change to the grain size and chemical compositions (of Ti, Nb and Zr) of the final alloy product. Therefore, a Ti alloy in accordance with the present disclosure has a grain size of 70-140 nm; preferably 75-135 nm, 80-130 nm, 85-125 nm; more preferably 90-120 nm, 100-100. The chemical compositions of the alloy are as defined above.

The microstructures of the nanostructured Ti alloy, as revealed by scanning electron microscopy, transmission electron microscopy or other equivalent microscopy techniques, contain two distinct regions: bcc beta-Ti and hcp alpha-Ti, with the bcc beta-Ti forming a matrix that surrounds the hcp alpha-Ti region. Microstructures of the Ti nanoalloy also clearly show that the alloy lacks the metastable, high-pressure and hexagonal omega phase. The nanoscale, ultra-fine grains of the alloy have an equiaxed structure, having approximately equal dimensions in all directions. The equiaxed grain structure contributes to high mechanical strength and low modulus more than acicular and lamellar structures.

Vickers hardness tests are performed on the produced Ti nanoalloys. In some embodiments, the Vickers hardness tests comply with at least one of the ASTM E92 Standard Test Method for Vickers Hardness of Metallic Materials, the ASTM E384 Standard Test Method for Microindentation Hardness of Materials, which are incorporated herein by reference in their entireties. The Ti nanoalloys have a microhardness or Vickers hardness of of 650-675 HV, preferably 655-675 HV, more preferably 655-660 HV, 660-665 HV, 665-670 HV and 670-675 HV.

The Ti nanoalloys of the present disclosure also possess high fracture stress, having Young's modulus values of 90-140 GPa, preferably 95-135 GPa, 100-130 GPa, more preferably 105-125 GPa, 110-120 GPa. These modulus values are significantly lower than the CoCr (Cast) and AISI 316L alloys. The Ti nanoalloys of the present disclosure corrosion resistant, biocompatibile, and has higher wear resistance and durability compared to the Ti-6Al 4V alloy, therefore making them suitable for various biomedical and dental implant applications. As used herein, the terms "tensile modulus", "Young's modulus", "elastic modulus" and simply "modulus" refer to a measure of the stiffness of a material defined as the ratio of the stress (force per unit area) along an axis to the strain (ratio of deformation over initial length). Modulus of elasticity can be measured by nanoindentation or compression tests such as the ASTM E9-09 Standard Test Methods of Compression Testing of Metallic Materials at Room Temperature (incorporated herein by reference in its entirety).

An embodiment of the present disclosure relates to apparatuses and devices whose entireties or at least a part thereof is composed of the nanostructured Ti alloy presented herein, including but not limited to biomedical, orthopedic and dental implants. Such parts include but are not limited to pins, rods, screws plates, nails, wires, bars, posts, films and coatings. Examples of biomedical implants incorporating the Ti alloy include but are not limited to artificial pacemaker, coronary stent, contraceptive implant (intrauterine device or IUD), cochlear implant, mechanical heart valve, expandable rib cage, spinal fusion cage and maxio-facial prosthetics. A non-exhaustive list of orthopedic implants with the Ti alloy of the present disclosure include Austin-Moore prosthesis, Baksi's prosthesis, Buttress plate, Charnley prosthesis, condylar blade plate, Ender's nail, Grosse-Kempf nail, Harrington rod, Hartshill rectangle, Insall Burstein prosthesis, interlocking nail, Kirchner wire, Kunscher nail, Luque rod, Moore's pin, Neers' prosthesis, rush nail, Smith Peterson nail, Smith Peterson nail with McLaughlin's plate, Seidel nail, Souter's prosthesis, Steffee plate, Steinmann pin, Swanson prosthesis, Talwalkar nail, Thompson prosthesis, total hip replacement system, hip resurfacing system, total knee replacement system, finger or toe replacement system, shoulder/ankle/elbow replacement system, femoral nail and tibial nail. Dental implants incorporating the Ti alloy described herein include but are not limited to root-form implant, Ramus-frame implant, transosseous implant and blade form implant.

Another embodiment relates to surgical instruments or devices that are made of the biomedical grade Ti nanoalloy of the present disclosure. Examples of these titanium surgical devices include but are not limited to surgical forceps, retractors, suture instruments, surgical tweezers, scissors, needle and micro needle holders, dental scalers, dental elevators, dental drills, endodontic files and reamers, Lasik eye surgery equipment, laser electrodes and vena cava clips.

A fabrication process of the Ti—Nb—Zr ternary alloy involving mechanical alloying/powder metallurgy and spark plasma sintering is further illustrated by the following example, which is not intended to limit the scope of the appended claims.

Example 1

Preparation of Ti-20Nb-13Zr at. % Near Beta Alloy

Elemental powders of titanium, niobium and zirconium were used as starting materials. The Ti, Nb and Zr powders were mixed in atomic percentage of Ti-20Nb-13Zr. The powder mixture then loaded in tungsten carbide vials with tungsten carbide balls to give a ball to powder ratio of 10:1 without the addition of a process control agent. The powders were mechanically alloyed (MA) for 10 h under argon atmosphere in a planetary ball mill (Fritsch Pulverisett 5) at room temperature with a rotational speed of 300 rpm. The MA powder was sintered using the spark plasma sintering (SPS) machine (FCT system-model HP D5, Germany).

The mechanically alloyed nanocrystalline Ti-20Nb-13Zr powders for 10 h were loaded into 20 mm graphite die and punched. A thin graphite foil was used between the powders and the die to facilitate sample ejection after sintering and to reduce the friction between the die walls and the powders. The SPS experiments were conducted in a vacuum atmosphere at a pressure of 50 MPa. The heating rate and holding time were selected to be 100 K/min and 10 min, respectively. The sintering temperatures were chosen to be 1000, 1100, and 1200° C.

Figure 2:
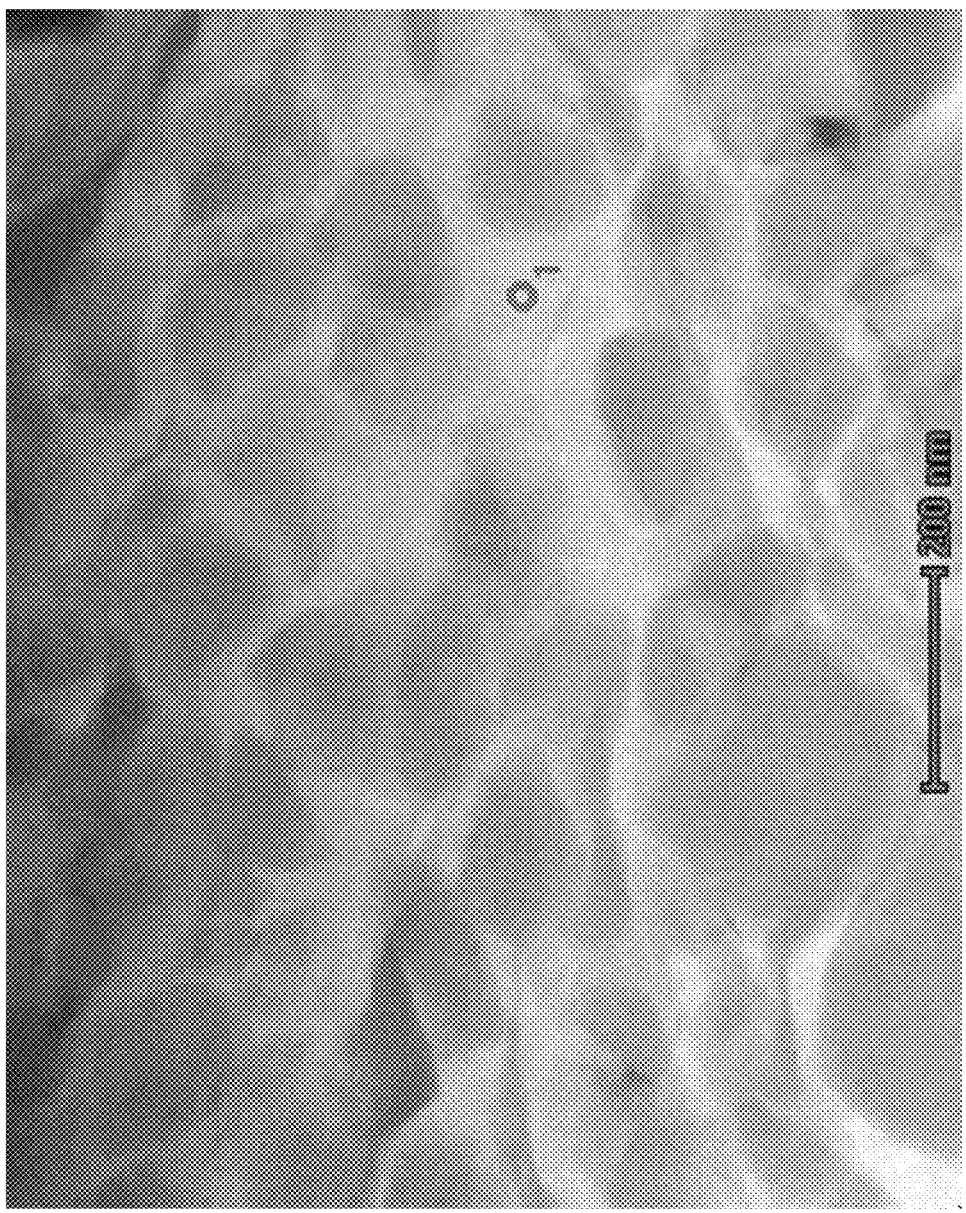
FIG. 2 is a TEM image of the nanostructured titanium alloy of FIG. 1A.

FIGS. 1A and 1B are FE-SEM images of the produced nanostructured Ti alloy at different magnifications while FIG. 2 is a TEM image of the Ti nanoalloy. These micrographs reveal that after spark plasma sintering, the alloy is chemically homogenized and the alloy microstructure is composed of body centered cubic (bcc) matrix in the beta phase and an alpha-Ti hexagonal closed packed (hcp) region surrounded by the bcc matrix. The Ti nanoalloy produced herein, as shown in FIGS. 1A, 1B and 2, exhibits an equiaxed structure (i.e. having grains with axes of approximately the same length) which has been reported to possess a better combination of high strength and low modulus than the acicular and lamellar structures.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. An alloy comprising:
20-22 at. % niobium;
12-13 at. % zirconium; and
≤68 at. % titanium;
wherein the alloy comprises an equiaxed granular structure with an average grain size of 70-140 nm;
wherein the equiaxed granular structure comprises a body centered cubic beta-titanium phase forming a matrix surrounding a hexagonal close packed alpha-titanium phase region; and
wherein the alloy is prepared by a process comprising:
providing an elemental powder mixture comprising 20-22 at. % niobium elemental powder, 12-13 at. % zirconium powder and ≤68 at. % titanium powder;
grinding the elemental powder mixture with a grinder comprising a grinding media to form a homogeneous alloy powder; and
spark plasma sintering the homogeneous alloy powder to produce the alloy.

2. The alloy of claim 1, wherein the alloy comprises:
20 at. % niobium;
13 at. % zirconium; and
≤67 at. % titanium.

3. The alloy of claim 1, wherein the alloy is a ternary alloy and is substantially free of an additional fourth element.

4. The alloy of claim 1, wherein the elemental powder mixture is ground at a weight ratio of the grinding media to the elemental powder mixture of 8:1 to 10:1.

5. The alloy of claim 1, wherein during the grinding, the grinder is agitated at 240-360 rpm.

6. The alloy of claim 1, wherein the grinding is carried out for 10-60 h.

7. The alloy of claim 1, wherein the spark plasma sintering is carried out at 50-100 MPa, 1000° C. to 1200° C. for 5-15 min.

8. The alloy of claim 1, being substantially free of an omega-titanium phase.

9. The alloy of claim 1, having a microhardness of 650-675 HV.

10. The alloy of claim 1, having a modulus of 90-140 GPa.

11. A device comprising the alloy of claim 1.

12. The device of claim 11, wherein the device is selected from the group consisting of a biomedical implants, an orthopedic implant, a dental implant, a surgical instrument and parts thereof.

* * * * *